United States Patent [19]

Bilski et al.

[11] Patent Number: 4,764,361
[45] Date of Patent: Aug. 16, 1988

[54] PHARMACEUTICAL COMPOSITIONS

[75] Inventors: Andrew J. T. Bilski, Congleton; Ralph Howe, Macclesfield; Balbir Rao; David S. Thomson, both of Holmes Chapel, all of England

[73] Assignee: Imperial Chemical Industries PLC, London, England

[21] Appl. No.: 24,568

[22] Filed: Mar. 11, 1987

[51] Int. Cl.$^4$ .............................................. A61K 31/00
[52] U.S. Cl. ...................................... 424/45; 514/596; 514/597; 514/613; 514/617; 514/619; 514/740; 514/741; 514/743; 514/758; 514/886; 514/887; 514/937; 514/944; 514/945; 514/969
[58] Field of Search .................. 424/45; 514/596, 597, 514/613, 617, 619, 740, 741, 743, 758, 886, 887, 937, 944, 945, 969

[56] References Cited

U.S. PATENT DOCUMENTS

| | | | |
|---|---|---|---|
| 3,933,911 | 1/1976 | Main | 514/630 |
| 3,944,611 | 3/1976 | Smith | 514/630 |
| 3,957,870 | 5/1976 | Main | 260/501.17 |
| 4,034,112 | 7/1977 | Smith | 514/524 |
| 4,041,074 | 8/1977 | Main | 260/501.19 |
| 4,117,157 | 9/1978 | Smith | 514/522 |

Primary Examiner—Morton Foelak
Assistant Examiner—S. A. Acquah
Attorney, Agent, or Firm—Cushman, Darby & Cushman

[57] ABSTRACT

The invention includes novel pharmaceutical compositions for topical use in the therapy or prophylaxis of inflammatory skin diseases, a method of treating one or more such diseases, a novel, optically active N-substituted-isobutyramide as an active ingredient and a process for the manufacture of said novel active ingredient.

10 Claims, No Drawings

PHARMACEUTICAL COMPOSITIONS

The invention concerns novel pharmaceutical compositions for topical use in the therapy or prophylaxis of inflammatory conditions affecting the skin of warm-blooded animals, including man. The invention also includes a novel therapeutic or prophylactic method for treating inflammatory skin conditions which method involves the administration of a non-steroidal active ingredient, previously only described for potential use in the treatment of heart disease. The invention also includes a novel, optically active ingredient for said composition and a process for its manufacture.

According to the invention there is provided a pharmaceutical composition adapted for topical administration which comprises as active ingredient the compound N-(2-[2-hydroxy-3-phenoxypropyl]aminoethyl)isobutyramide of formula I (set out hereinafter), in racemic (R,S) or laevorotatory optically active (S) form, or a pharmaceutically acceptable acid-addition salt thereof, (hereinafter referred to as the compound of formula I), together with a dermatologically suitable diluent or carrier.

The racemic (R,S) form of the compound of formula I is described, inter alia, as its free base as a cardioselective beta-adrenergic blocking agent in our UK patent specification Ser. No. 1455116, as is the oxalate salt of the corresponding (−)- or laevorotatory optically active (S) form. The crystalline free base form of the latter laevorotatory optically active form of the compound of formula I and crystalline and 2,3:4,6-di-o-isopropylidene-α-D-xylo-hexulosofuranosonate salts thereof (other than the oxalate) have not hitherto been described and are provided as a further feature of the invention, based on their unexpected activity as topical anti-inflammatory agents. UK patent specification Ser. No. 1455116 also describes a range of pharmaceutical compositions suitable for oral or parenteral use for effects on the vascular system. However, there is no mention in said specification of anti-inflammatory effects or any description of compositions specifically adapted for topical administration such as ointments, gels, creams or lotions. The invention also provides the use of the compound of formula I in racemic (R,S) or laevorotatory optically active (S) form, or of a pharmaceutically acceptable salt thereof, in the manufacture of a novel medicament agent for the treatment or prophylaxis of inflammatory conditions of the skin affecting warm-blooded animals, including man.

It is to be understood that the term laevorotatory optically active form means the form having a negative specific optical rotation measured in methanol at a wavelength of 589 nm i.e. at the D line of the sodium vapour emission spectrum.

Examples of suitable forms of pharmaceutical compositions adapted for topical use and within the scope of the invention include ointments, creams, gels, salves and lotions. In addition, the compound of formula I may also be administered topically by spray or aerosol direct to or adjacent to the affected area of the skin. Typical compositions of the invention will contain, for example, up to 10% by weight of the compound of formula I and, preferably from 0.1 to 5% by weight.

Examples of dermatologically suitable diluents or carriers include those well known in the art of pharmacy for the production of topical formulation, such as non-volatile fatty alcohols, acids and/or esters (e.g. cetostearyl alcohol, cetyl alcohol, stearyl alcohol, stearic acid or cetyl esters wax); volatile alcoholic compounds [e.g. (1–4C)alkanols such as ethanol or propanol]; glycols and glycol ethers (e.g. propylene glycol or ethyl digol); glycerol and glycerol ethers; emulsifying agents (e.g. sorbitan stearate, sorbitan trioleate, polysorbate 60 or a mixture of polyoxyethylated oleyl or cetyl alcohol); preservatives (e.g. (1–4C)alkyl hydroxybenzoates such as methyl or propyl hydroxybenzoates); and non-volatile hydrocarbons such as soft paraffin or liquid paraffin. Illustrative formulations are provided in the accompanying Examples.

The topical formulations of the invention may be made by methods well known in the art for the production of topical formulations, using conventional, pharmaceutically acceptable excipients. Thus, a particular ointment formulation may be prepared by dispersing an active ingredient as defined above in a suitable organic diluent, for example soft paraffin, optionally in the presence of an emulsifying and/or thickening agent, for example sorbitan monostearate.

A particular gel formulation may be prepared by adding a gelling agent, for example neutralised carboxypolymethylene, to a solution of an active ingredient as defined above in a suitable organic solvent, for example 2-propanol.

A particular emulsion formulation, for example a cream or a lotion, may be prepared by mixing an active ingredient as defined above with a suitable conventional emulsifying system and water.

The topical formulations are conveniently provided for therapeutic or prophylactic treatment of inflammatory skin conditions packaged in dispensers such as deformable tubes containing for example, 15 to 250 g of formulation and such filled dispensers are provided as a further feature of the invention.

An example of a suitable pharmaceutically acceptable acid-addition salt is, for example, a hydrohalide salt such as a hydrochloride or hydrobromide, or a salt with a suitable organic acid, such as a citrate or D-gluconate salt.

In general, it is preferred to use the laevorotatory optically active (S) form of the compound of formula I, that is (S)-N-(2-[2-hydroxy-3-phenoxypropyl]aminoethyl)isobutyramide, as the free base or as a pharmaceutically acceptable acid-addition salt thereof in the formulation and methods of the invention.

The compound of formula I may be obtained in laevorotatory optically active form by resolution of the racemic form with 2,3:4,6-di-O-isopropylidene-α-D-xylo-hexulofuranosonoic acid, using the procedure described in UK patent specification Ser. No. 1455116. Alternatively, it may be prepared directly by reaction of (S)-1,2-epoxy-3-phenoxypropane with N-(2-aminoethyl)isobutyramide, conveniently in a suitable solvent or diluent, for example a (1–4C)alkanol such as ethanol at a temperature in the range, for example 40°–140° C., and subsequently converted, if required, to the appropriate salt by reaction with the corresponding acid. Such a procedure is provided as a further feature of the invention.

The production of the novel free base and hydrochloride salt form of the laevorotatory optically active form of the compound of formula I is described in the accompanying Examples.

The unexpected topical anti-inflammatory effects of the compound of formula I may be demonstrated, for example, in a number of routine tests in laboratory animals:

(a) in a standard test involving the inhibition of inflammation on the mouse ear induced by the irritant, croton oil (Test A);

(b) in a standard test involving the inhibition of the delayed hypersensitivity reaction to the contact irritant, 4-ethoxymethylene-2-phenyloxazolone (hereinafter referred to as oxazolone) in mice (Test B); and (c) in a standard test involving oxazolone induced contact dermatitis in the domestic pig (Test C).

Summarised test procedures and typical results with the compound of formula I are given in the Examples hereinafter, and demonstrate the topical anti-inflammatory properties of the racemic (R,S) and laevorotatory (S) optically active forms at low application rates, for example they have $ED_{50}$ application rates of 44 and 29 micrograms/ear, respectively, in Test A. By contrast, the dextrorotatory, optically active (R) form of compound I, the known beta-adrenergic blocking agent propranolol and the known, structurally related, partial beta-adrenergic cardiac stimulant xamoterol (described by H F Marlow et alia, British J. Clin. Pharm., 1982, 13, 269–270P) are all inactive as topical anti-inflammatory agents when administered at application rates of 250 micorgrams/ear in Test A.

In addition, because of its intrinsic beta-adrenergic pharmacological profile, the compound of formula I causes no adverse effects on the cardiovasculature even when large doses are administered topically to the skin.

It is envisaged that the compound of formula I will be of value in the treatment of both acute and chronic inflammatory diseases or inflammatory conditions affecting the skin of warm-blooded animals (including man), for example in psoriasis, eczema, urticaria, contact dermatitis, atopic dermatitis, inflammatory dermatoses, sun-burn and insect bites, as a result of its particular combination of topical anti-inflammatory properties. In addition the compound of formula I is expected to be of value in treating such conditions in warm-blooded animals (especially man) where sensitisation to, or adverse reactions from, the use of steroids has occurred or is likely to occur. However, the compound of formula I will generally be used in the treatment of inflammatory diseases or inflammatory conditions affecting the skin in an analogous manner to that in which known topically active anti-inflammatory agents, for example the topically active steroids, such as hydrocortisone, fluocinolone acetonide or betamethasone-17-valerate, are used. One or more such agents and/or other pharmaceutical agents known to be useful in treating inflammatory diseases or conditions of the skin may be used in addition to the compound of formula I in the methods of the invention or included in compositions of the invention.

When used for the topical treatment of an area of inflammation affecting the skin of a warm-blooded animal, for example man, the compound of formula I may be administered topically at a dose in the range 10 micrograms to 1 mg/cm$^2$, or at an equivalent dose of a pharmaceutically acceptable acid-addition salt thereof, and, if necessary, a dose in this range may be repeated at intervals of, for example 4–12 hours. However, it will be appreciated that the total daily amount of compound of formula I administered necessarily depends on the age and sex of the patient and the extent and severity of the inflammatory disease or condition under treatment, and will be varied in accordance with normal medical practice.

The invention is illustrated, but not limited, by the following Examples in which Examples 1 and 2 describe the production of, respectively, the novel free base and hydrochloride salt forms of the laevorotatory form of the compound of formula I, Example 3 describes the topical anti-inflammatory properties of the compound of formula I in Tests A, B and C, and Examples 4 and 5 describe illustrative topical formulations of the invention. In addition, Example 6 describes the production of the laevorotatory form of the compound of formula I without intermediate production of the racemic form.

EXAMPLE 1

A mixture of (−)-N-[2-hydroxy-3-phenoxypropyl]-N-(2-isobutyramidoethyl)ammonium 2,3:4,6-di-O-isopropylidene-α-D-xylo-hexulosofuranosonate [also known as (−)-1-phenoxy-3-β-isobutyramidoethylamino-2-propanol (−)-2,3:4,6-di-O-isopropylidene-2-keto-L-gulonate and described in Example 31 of UK patent specification Ser. No. 1455116] (96 g) and 2M sodium hydroxide solution (500 ml) was extracted with methylene chloride (200 ml). The extracts were dried (MgSO$_4$) and the solvent evaporated. The residue was recrystallised twice from ethyl acetate to give crystalline (−)-N-(2-[2-hydroxy-3-phenoxypropyl]aminoethyl)isobutyramide as a white solid, m.p. 89°–91° C., $^{25}[\alpha]_D$ −6.3° [c, 1.05; methanol]; microanalysis, $C_{15}H_{24}N_2O_3$ requires: C, 64.3; H, 8.60; N, 10.0%; found: C, 64.4; H, 8.5; N, 9.8%.

EXAMPLE 2

A solution of (−)-N-(2-[2-hydroxy-3-phenoxypropyl]aminoethyl)isobutyramide (0.7 g) in anhydrous ether (10 ml) was treated with an excess of a saturated solution of hydrogen chloride in anhydrous ether. The solid which formed was collected and recrystallised twice from a mixture of methanol and anhydrous ether to give (−)-N-[2-hydroxy-3-phenoxypropyl]-N-(2-isobutyramidoethyl)ammonium chloride, m.p. 137°–139° C; $^{25}[\alpha]_D$ −19.7° [c, 1.135; methanol]; microanalysis $C_{15}H_{24}N_2O_3$·HCl requires: C, 56.87; H, 7.90; N, 8.84; Cl, 11.20%; found: C, 56.80; H, 8.0; N, 8.6; Cl, 11.1%.

EXAMPLE 3

1-Test A (a) Method: Groups of mice were dosed with an acetone solution of test compound or vehicle (acetone) pre-mixed with an equal volume of 4% w/v croton oil in acetone topically to the right ear (10 μl volume). Four hours later, the animals were killed and both the left (control) and right (treated) ears were removed and weighed. The percentage increase in ear weight of the treated against control was then calculated. The anti-inflammatory activity was finally expressed as percentage inhibition for the test compound dosed group in comparison with the vehicle dosed control group.

(b) Results: Using the free base form of the compound of formula I as its racemic (R,S) or (−)-optically active (S) form, the following results were obtained in Test A:

| Test Compound | Dose (μg/ear) | Number of animals | % increase in in ear weight ± SEM | % Inhibition | $ED_{50}$ |
| --- | --- | --- | --- | --- | --- |
| racemate | 0 | 10 | 79.4 ± 5.32 | — | |
| | 2.5 | 10 | 59.1 ± 5.92 | 25.6 | |
| | 25 | 10 | 40.2 ± 4.88 | 49.3 | 44 |
| | 250 | 9 | 30.3 ± 4.0 | 61.8 | |
| (−)-(S) form | 0 | 61 | 85.6 ± 2.53 | — | |
| | 4.9 | 30 | 65.2 ± 3.17 | 23.8 | |
| | 14.8 | 30 | 45.8 ± 3.96 | 46.5 | 29 |
| | 44.4 | 30 | 40.9 ± 4.02 | 52.2 | |
| | 133.3 | 30 | 28.6 ± 3.56 | 66.5 | |
| | 400 | 30 | 7.0 ± 1.25 | 91.8 | |

Under similar test conditions hydrocortisone shows approximately 70% inhibition when applied at a dose of 25 μg/ear.

2-Test B (a) Method: Mice were sensitised by the topical application of a 10 μl portion of a 0.5% w/v solution of oxazolone in acetone. After 7 days, a 10 μl portion of a solution of the test compound in acetone (acidified to pH 5 with citric acid*) or, for control purposes, just the acidified acetone vehicle, was applied to the right ears of the mice and immediately followed by an application of 10 μl of 0.5% w/v solution of oxazolone in acetone. After 24 hours the animals were killed, the ears removed and results calculated as for Test A above.
*Note: acidified acetone was used to eliminate any possible reaction between the basic test compound of formula I and the oxazolone.]

(b) Results: Using the free base form of the (−)-optically active (S) form of the compound of formula I, the following results were obtained:

| Dose (μg/ear) | Inhibition (%) |
| --- | --- |
| 2.5 | 20 ± 8 |
| 25 | 35 ± 9 |
| 250 | 60 ± 7 | from which the $ED_{50}$ of 91 μg/ear may be calculated.

3-Test C

Method: Domestic pigs were sensitised by topical application of 0.4 ml of a 10% w/v solution of oxazolone in acetone to the neck region on two occasions two weeks apart. Six paired sites were then prepared and delineated with one site from each pair to the left and one to the right of the mid-line of the back of the animal. The left hand site of the first three pairs was then treated with 0.05 ml of a first solution of the test compound in acetone (acidified to pH 5 with citric acid). The left hand site of the second three pairs was similarly treated with 0.05 ml of a second solution of the test compound in acetone at pH 5. All of the righthand sites were used as controls and were treated with 0.05 ml of acetone (acidified to pH 5 with citric acid). After 24 hours, the same treatment was repeated followed immediately by a challenge of 0.025 ml of a 1% w/v solution of oxazolone in acetone to the 1st and 4th pairs of sites, of 5% w/v solution of oxazolone in acetone to the 2nd and 5th pair of sites, and of 10% w/v solution of oxazolone in acetone to the 3rd and 6th pairs of sites. After 36 hours, the area and degree of erythema were measured (the latter using a simple electrical device for measuring erythema by assessing the amount of green light reflected from the skin as detected by a photocell, for example as is described in UK patent specification Ser. No. 2103359B). An inflammatory index was obtained by multiplying the area and erythema readings together. By comparison of the values for the treated and control sites, the percentage reduction in erythema of the test compound could be assessed.

(b) Results: As different effects were obtained at different concentrations of the oxazolone challenge, the results were expressed as the percentage of responses which resulted in a given degree of reduction in erythema (i.e. 30%, 50% or 70% reduction in erythema). Thus 50 at 30% means that half of the test sites showed at least a 30% inhibition of erythema. The following results were obtained using a 2% w/v solution of the free base form of the (−)-optically active (S) form of the compound formula I in acetone (acidified to pH 5 with citric acid):

| Experiment No. | No. of pigs | % of sites in which erythema is inhibited by: | | |
| --- | --- | --- | --- | --- |
| | | 30% | 50% | 70% |
| 1 | 2 | 80 | 60 | 20 |
| | | 73 | 36 | 9 |
| 2 | 2 | 50 | 50 | 17 |
| 3 | 2 | 83 | 67 | 17 |
| Average | | 71 | 53 | 16 |

Using the same test procedure but applying as test treatments a 1% w/v solution of hydrocortisone (HC) or betamethasone-17-valerate (BV) in a mixture of aqueous ethanol containing 40% w/v N-methylpyrrolidone (as the test vehicle: TV), the following results were obtained:

| Test Compound | No. of pigs | % of sites in which erythema is inhibited by: | | |
| --- | --- | --- | --- | --- |
| | | 30% | 50% | 70% |
| HC | 18 | 67 | 28 | 6 |
| BV | 8 | 75 | 38 | 25 |
| TV | 8 | 0 | 0 | 0 |

Similarly, using the cream formulation II, described in Example 4 hereafter (which is adjusted to pH 5 by addition of citric acid) the following results were obtained with the free base form of the (−)-optically active (S) form of the compound of formula I:

| No. of pigs | Concentration of test compound (% w/w) | % of sites in which erythema is inhibited by: | | |
| --- | --- | --- | --- | --- |
| | | 30% | 50% | 70% |
| 3 | 0.25 | 86 | 29 | 14 |
| 4 | 0.5 | 86 | 29 | 29 |
| 3 | 1 | 88 | 75 | 50 |
| 2 | 2 | 100 | 80 | 80 |

Note: no overt toxic or adverse effects were observed with the compound of formula I during the above test.

EXAMPLE 4

(Components given in % w/w unless otherwise stated.)

Typical pharmaceutical compositions of the compound of formula I in a form suitable for topical administration may be obtained by conventional procedures and with the following constitutions:

| Cream Formulation I | |
| --- | --- |
| Active ingredient | 1–2.5 |
| Cetyl esters wax (Synthetic spermaceti) | 1.0 |
| Glycerol | 1.0 |
| Cetostearyl alcohol | 4.0 |
| 'Span' 60 (Sorbitan stearate) | 2.0 |
| 'Tween' 60 (Polysorbate 60) | 2.0 |
| Ethanol 96% BP | 3.0 v/w |
| Methyl hydroxybenzoate | 0.15 |
| Propyl hydroxybenzoate | 0.08 |
| Purified water | to 100% |

| Ointment Formulation I | |
| --- | --- |
| Active ingredient | 1–2.5 |
| Ethyl digol | 5.0 |
| Ethanol 96% BP | 3.0% v/w |
| Purified water | 2.0 |
| 'Span' 85 (Sorbitan trioleate) | 3.0 |
| White soft paraffin | to 100% |

| Lotion Formulation I | |
| --- | --- |
| Active ingredient | 1–2.5 |
| Propylene Glycol | 5.0 |
| Cetostearyl alcohol | 3.0 |
| 'Lubrol' 17A17* | 0.6 |
| Methyl hydroxybenzoate | 0.15 |
| Propyl hydroxybenzoate | 0.08 |
| Purified water | to 100% |

*polyoxyethylated oleyl/cetyl alcohol containing an average of 17 ethoxylate groups per molecule [Note: 'Span', 'Tween' and 'Lubrol' are trade marks].

| Cream Formulation II | |
| --- | --- |
| Active ingredient | 2.0 |
| Citric Acid | 0.7 |
| Cetyl esters wax | 2.0 |
| Cetostearyl alcohol | 4.0 |
| 'Lubrol' 17A17 | 1.0 |
| Light liquid paraffin | 3.0 |
| 'Arlacel' 165* | 3.0 |
| Butylated hydroxytoluene | 0.05 |
| Phenoxyethanol | 1.0 |
| Purified water | to 100% |

[*'Arlacel' (trade mark) is a brand of acid-stable, self-emulsifying monostearin (glyceryl stearate + PEG 100 stearate), available from ICI Speciality Chemicals.]

Similarly, when cream formulations II are required with 1.0, 0.5 or 0.25% active ingredient, the same components as described above are used except that 0.35, 0.175 or 0.088% citric acid is required.

All of the cream formulations II had a final pH of about 5.4. "Lubrol" 17A17 may be replaced by an alternative excipient such as 'Brij' (trade mark) 78, also known as steareth 20.

EXAMPLE 5

(Components given in % w/w unless otherwise stated.)

| Cream Formulation III | |
| --- | --- |
| Active ingredient | 0.5–2.5 |
| Cetostearyl alcohol | 6.0 |
| Cetyl esters wax | 3.0 |
| Light liquid paraffin | 4.0 |
| 'Brij' 78 | 1.0 |
| 'Arlacel' 165 | 1.1 |

| -continued | |
| --- | --- |
| Cream Formulation III | |
| Phenoxyethanol | 1.1 |
| Butylated hydroxytoluene | 0.1 |
| Purified water | to 100% |

Cream Formulation IV

As formulation III, but phenoxyethanol replaced by methyl hydroxybenzoate (0.15) and propyl hydroxybenzoate (0.08).

Cream Formulation V

As formulation III, but 'Brij' 78 replaced by 'Brij' 58 (ceteth 20)

| Ointment Formulation II | |
| --- | --- |
| Active ingredient | 2–5 |
| Light liquid paraffin | 10–20 |
| White soft paraffin | to 100% |

[Note: In the above cream, ointment and lotion formulations in Exs. 4 and 5, the active ingredient may be the (−)-optically active (i.e. laevorotatory) (S) form or the racemic (R,S) form of the compound of formula I, either as the free base or as a pharmaceutically acceptable salt, the latter being conveniently formed in situ during the formulation procedure by incorporating the appropriate amount of acid into the excipients, for example as described for Cream II above. In general, those formulations which contain the (−)-optically active (S) form of the compound of formula I are preferred for medical or veterinary use in treating inflammatory diseases and/or conditions affecting the skin of warm-blooded animals such as man and valuable domestic animals. The formulations may be made by standard procedures well known in the pharmaceutical art and quantities of individual excipients may be varied to obtain formulations of optimum stability and appearance.

EXAMPLE 6

A mixture of (S)-1,2-epoxy-3-phenoxypropane (0.495 g.) and N-(2-aminoethyl)isobutyramide (0.429 g) in ethanol (25 ml) was heated under reflux for 48 hours. The reaction mixture was cooled and solvent removed by rotary evaporation in vacuo. The residual solid was purified by column chromatography on silica (Merck, Art. 7736) using 5% v/v methanol in dichloromethane as eluant. The solid thereby obtained was purified by recrystallisation from ethyl acetate to give (S)-N-(2-[2-hydroxy-3-phenoxypropyl]aminoethyl)isobutyramide (0.425 g), m.p. 88°–89° C., $^{24}[\alpha]_D$ −5.8° [c, 1.04; methanol], mixed m.p. with material from Example 1, 88°–89° C.

The starting (S)-1,2-epoxy-3-phenoxypropane may be obtained, for example, as described in European patent application, publication number 166527A2 or *J. Amer. Chem. Soc.*, 1970, 101(13), 3666–3668.

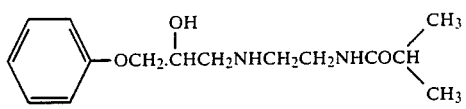

Formula I

What is claimed is:

1. A pharmaceutical composition adapted for topical administration which comprises as active ingredient the compound N-(2-[2-hydroxy-3-phenoxypropyl]aminoethyl)isobutyramide in racemic (R,S) or laevorotatory optically active (S) form or a pharmaceutically acceptable acid-addition salt thereof together with a dermatologically suitable diluent or carrier.

2. A composition as claimed in claim 1 which is in the form of an ointment, cream, gel, salve, lotion, spray or aerosol.

3. A composition as claimed in claim 1 which contains from 0.1 to 5% of active ingredient.

4. A composition as claimed in claim 1 in which the active ingredient is (S)-N-(2-[2-hydroxy-3-phenoxypropyl]aminoethyl)isobutyramide or a pharmaceutically acceptable acid-addition salt thereof.

5. A composition as claimed in claim 1 wherein, in the active ingredient, the pharmaceutically acceptable acid-addition salt is selected from hydrochloride, hydrobromide, citrate and D-gluconate salts.

6. A topical anti-inflammatory agent which comprises N-(2-[2-hydroxy-3-phenoxypropyl]aminoethyl)isobutyramide in racemic (R,S) or laevorotatory optically active (S) form, or a pharmaceutically acceptable acid-addition salt thereof.

7. A topical anti-inflammatory agent which comprises (S)-N-(2-[2-hydroxy-3-phenoxypropyl]aminoethyl)isobutyramide or a pharmaceutically acceptable acid-addition salt thereof.

8. (S)-N-(2-[2-Hydroxy-3-phenoxypropyl]aminoethyl)isobutyramide or a pharmaceutically acceptable acid-addition salt apart from an oxalate or 2,3:4,6-di-O-isopropylidene-α-D-xylo-hexulosofuranosonate salt.

9. A method of producing a topical anti-inflammatory effect in a warm blooded animal requiring such treatment, which comprises administering to said animal an effective amount of a therapeutic agent selected from N-(2-[2-hydroxy-3-phenoxypropyl]aminoethyl)isobutyramide in racemic (R,S) or laevorotatory optically active (S) form and the pharmaceutically acceptable salts thereof.

10. A pharmaceutical composition as claimed in claim 1 which contains in addition a topically active steroid.

* * * * *